United States Patent [19]

Brown

[11] Patent Number: 5,234,432
[45] Date of Patent: Aug. 10, 1993

[54] METHOD AND APPARATUS FOR DEFINITIVE CUTTING OF A FEMUR

[76] Inventor: Byron L. Brown, 2315 Hendricks, Fort Smith, Ark. 72903

[21] Appl. No.: 850,846

[22] Filed: Mar. 13, 1992

[51] Int. Cl.$^5$ .......................... A61B 17/00; A61F 5/00
[52] U.S. Cl. ........................................ 606/79; 606/86
[58] Field of Search ................ 606/82, 83, 84, 85, 606/86, 89; 403/319, 324, 331; 623/16–23

[56] References Cited

U.S. PATENT DOCUMENTS

| | | | |
|---|---|---|---|
| 4,357,716 | 11/1982 | Brown | 623/18 |
| 4,364,389 | 12/1982 | Keller | 606/86 |
| 4,601,289 | 7/1986 | Chiarizzo | 623/23 |
| 4,718,909 | 1/1988 | Brown | 623/16 |
| 4,834,080 | 5/1989 | Brown | 623/16 |
| 4,921,493 | 5/1990 | Webb | 606/85 |
| 4,963,155 | 10/1990 | Lazzeri | 606/86 |
| 5,037,425 | 8/1991 | Brown | 606/92 |
| 5,047,061 | 9/1991 | Brown | 606/92 |

Primary Examiner—Robert A. Hafer
Assistant Examiner—Michael Brown

[57] ABSTRACT

Method and apparatus for definitive cutting of the proximal end of a femur prior to cementing in a prosthesis. A special stem is temporarily inserted into the principal cavity within the femur to act as a support and guide for cutters. Provision is made within the proximal end of the stem for positioning of a pair of spindles which are successively used to make two precision cuttings of the upper surface of the intertrochanteric area of the bone by use of a rotational cutter. The cutter is first temporarily rotationally positioned on a first one of the spindles and is rotated thereon while the cutting head of the cutter is in contact with the area of the bone to be cut. The cutter is then transferred to the other spindle for rotation thereon while the cutting head of the cutter is in contact with another portion of the bone to be cut. Thereafter, the rotational cutter is removed and a rectilinear cutter is positioned on the stem using one of the spindles and another spindle substituted for the remaining original spindle, thereby providing a rigid support for the cutter that performs the rectilinear cutting.

22 Claims, 3 Drawing Sheets

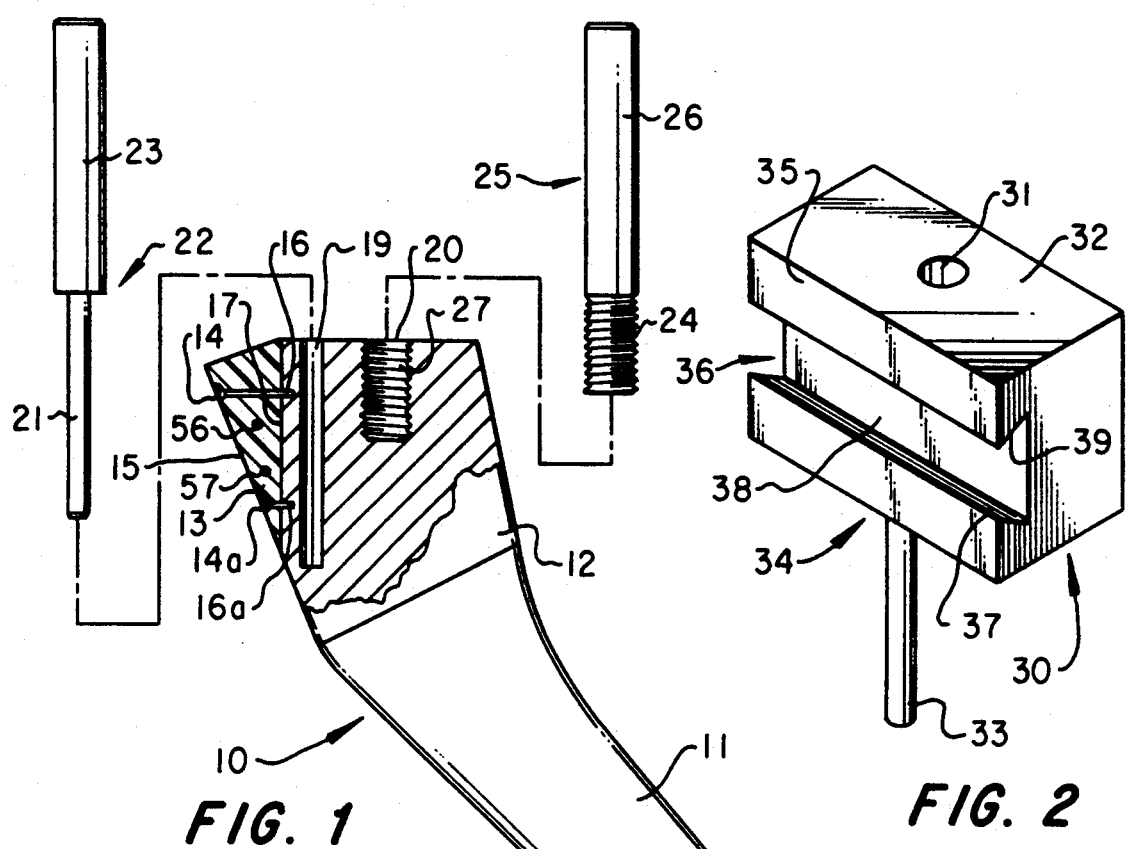
FIG. 1
FIG. 2
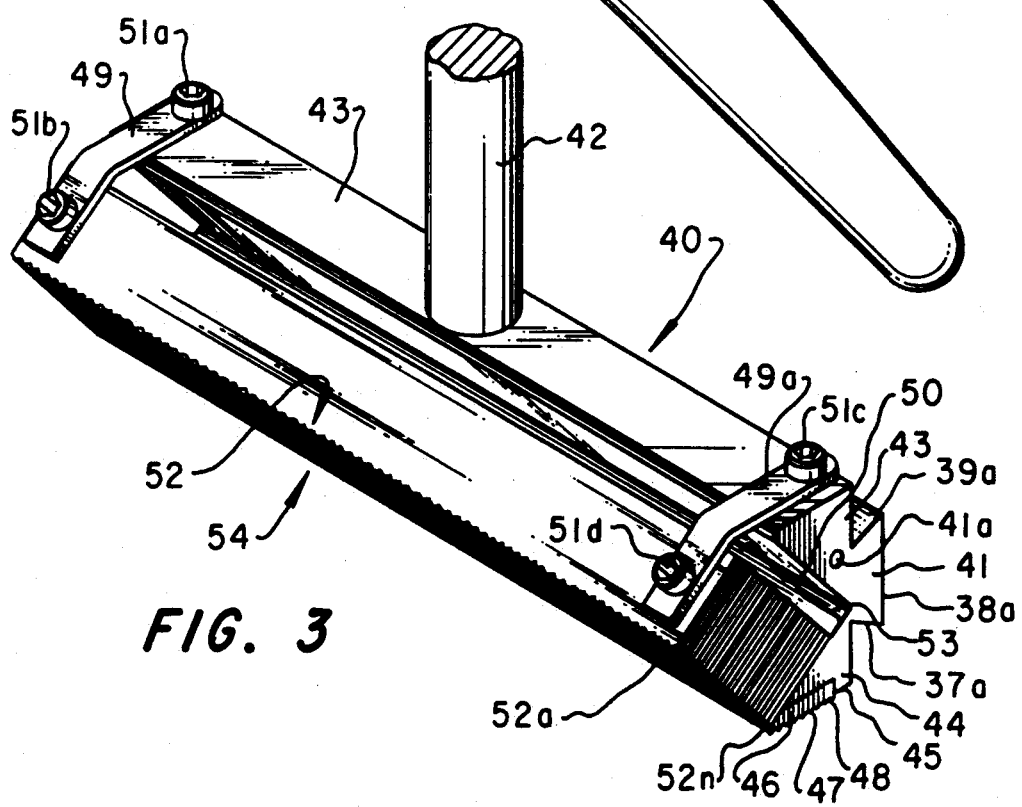
FIG. 3

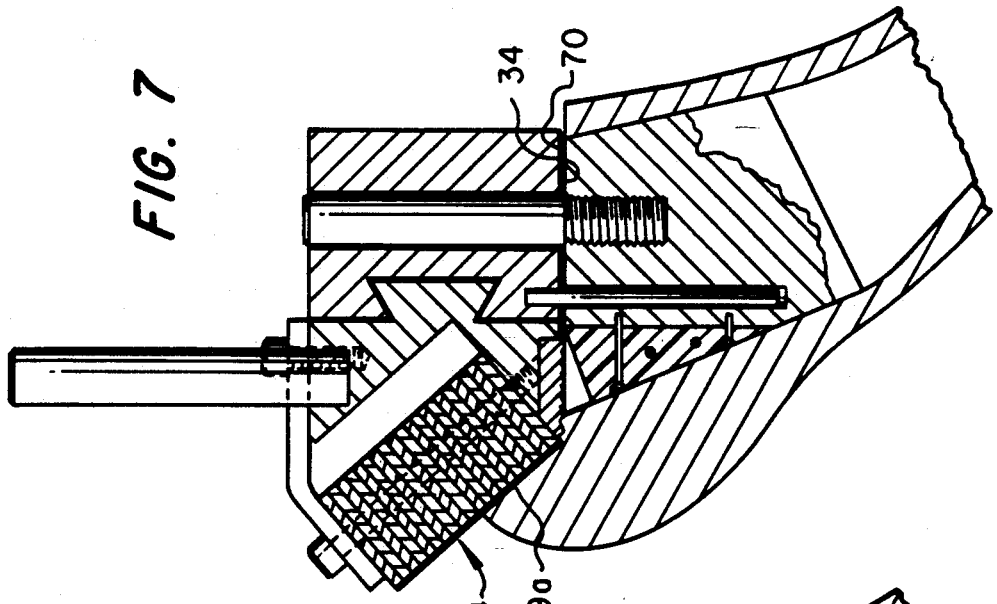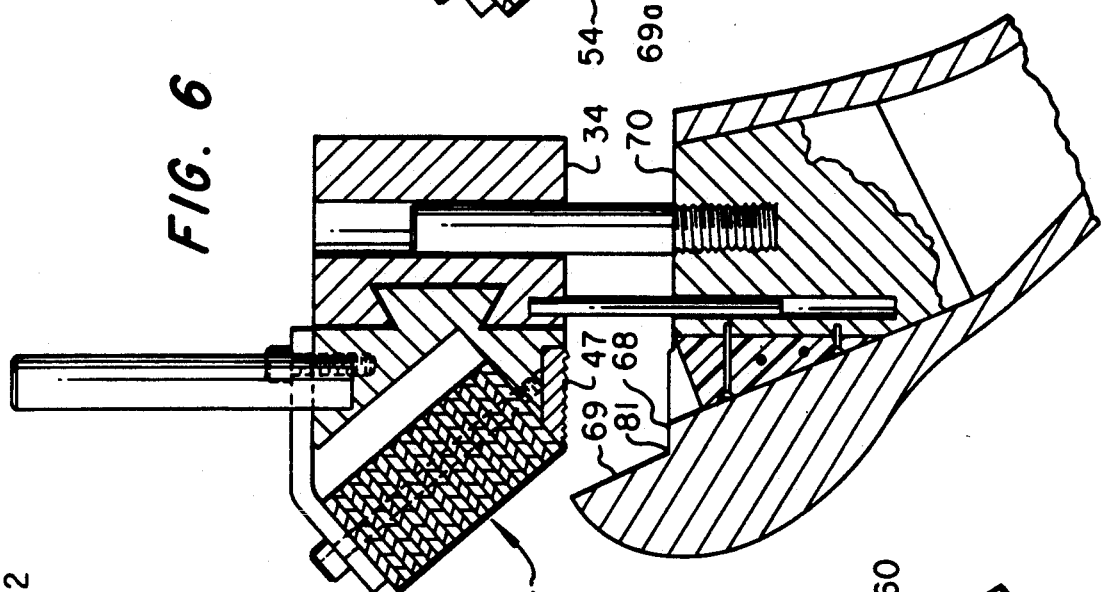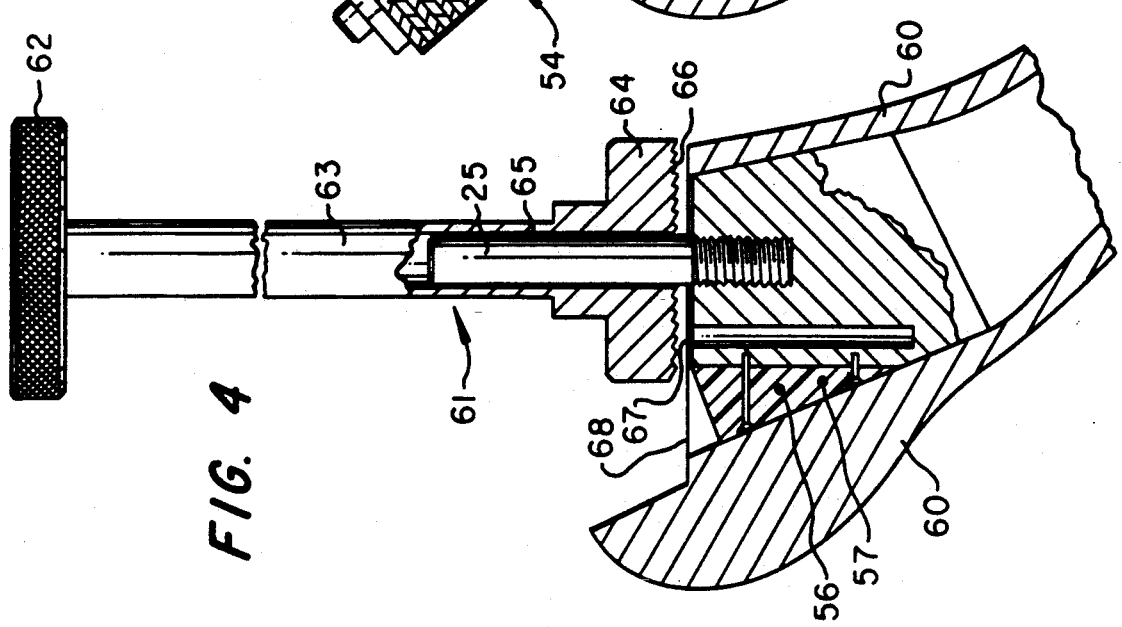

METHOD AND APPARATUS FOR DEFINITIVE CUTTING OF A FEMUR

This invention relates to the definitive cutting of the proximal end of a femur prior to cementing in a prosthesis.

BACKGROUND OF THE INVENTION

In modern hip reconstruction surgery, there is the necessity for preparing the femur for acceptance of a prosthesis. In the past, this has been accomplished in several ways including the removal of the head and a part of the neck of a femur using a conventional surgical saw, after which the exposed surfaces of the antero-medial aspect of the femur were dressed more precisely so as to properly engage a collar that typically extended about the upper part of the prosthesis. For details relating to the preparation of femurs and the installation of prostheses, reference is hereby made to the following U.S. Pat. No. 4,357,716 entitled "Device and Method for Cementing a Hip Prosthesis in a Femoral Canal", U.S. Pat. No. 4,718,909 entitled "Method and Apparatus for Cementing a Femoral Stem Prosthesis Within a Femoral Canal", U.S. Pat. No. 4,834,080 entitled "Drill Bit Guide", U.S. Pat. No. 5,037,425 entitled "Device and Method for Cementing a Hip Prosthesis in a Femoral Canal", and U.S. Pat. No. 5,047,061 entitled "Prosthesis Holder", the disclosures of which are hereby incorporated by reference.

One proposal of the prior art for accomplishing the more precise dressing of the antero-medial aspect of the femur involves the use of a circular cutter which is rotated about a spindle that is temporarily disposed in the desired position adjacent the exposed surfaces of the femur. However, the utilization of such prior art cutters has occasioned certain disadvantages. Thus, for example, if the diameter of the circular cutter is made sufficiently large to contact the entire work surface, it extends beyond the sides of the femur and undesirably engages adjoining tissue, thus causing undesired injury and trauma. On the other hand, if the diameter of the circular cutter is made sufficiently small so as to be limited to engagement with the work surface of the femur, it does not extend over the entire work surface.

Presently when a prosthetic stem is installed in a femoral canal, be it without cement or with cement, but without sustained pressure of the cement, the shaping and cutting of the proximal end of the femur is far less critical than when the cement is pressurized and the pressure sustained until the cement is mature. Presently with power saws which have attachments for cutting at various angles, the bone is usually cut and trimmed by "eye-balling". Such trimming is dependent upon the surgeon's skill of making an acceptable cut. In some instances the surgeon may elect to employ a single circular cutter which is positional on a single spindle mounted on a trial-like femoral stem.

U.S. Pat. Nos. 4,357,716; 4,718,909; 4,834,080; 5,037,425 and 5,047,061 relate to methods and apparatus for positioning the femoral stem prosthesis and pressurizing the bone cement in the femoral canal after the femur has been inserted and accurately positioned in the canal; and pressure is maintained until the cement has sufficiently set to maintain the prosthesis in place. In order to maintain pressure on the cement and stem, a seal must be developed at the cut surfaces of the proximal femur with a sealing mechanism. It is apparent that the cut surfaces must mate accurately with the sealing mechanism. And so, after the head and part of the neck have been removed, the surgeon employs a circular cutter to cut and define a portion of the antero-medial aspect of the femur and then attempts to evenly rasp the remaining portion of the horizontal cut with that of the antero-medial surface. Lastly, the surgeon defines the slope of the posterior cut with a rasp. The two cut planes must match the two planes of the sealing mechanism. The process of matching the cut surface of the bone with the sealing mechanism entails repeated trial raspings and is time consuming, and requires a great deal of accuracy. Also there exists the possibility of removing an excess amount of cortex in a given area, and so the method of employing sustained pressure after the stem has been inserted into the canal is abandoned and the stem is inserted into the cement without sustained pressure. This is unsatisfactory.

BRIEF SUMMARY OF THE INVENTION

The improvements according to the invention, provide improved apparatus and method that overcome the foregoing drawbacks of the prior art. This is accomplished by a combination of features that advantageously exploit the advantages of the small diameter circular rotational cutter with the advantages of a cooperative rectilinear cutter, thereby providing the surgeon with easily usable precision techniques which greatly facilitate the preparation of a femur for installation of a prosthesis.

An elongated prosthesis-like stem is provided for temporary positioning within the partially prepared femur. The stem includes at the upper end thereof, an essentially flat surface lying within a plane essentially at right angles to the adjacent longitudinal axis of the upper end of the stem. Extending at right angles from the essentially flat surface there are a pair of elongated cylindrical members which act as spindles and which have parallel axes spaced apart by a predetermined amount so as to permit the use of a small diameter circular cutter successively on both cylindrical spindles, thus providing for coverage of the desired femur work surface excepting for the ends of the horizontal cuts adjacent to the cuts of the posterior slope.

To complete the precision dressing of the work surface of the femur, after the aforementioned successive use of the small diameter rotational cutter, the rotational cutter is removed. Two spindles are utilized sa mounts for the temporary mounting of a linearly grooved positioning block. The linearly grooved positioning block is adapted for mated fitting with a rectilinear cutter which has a linear elongated projection that is form-fitted to the groove so that the grove acts as a guide for the rectilinear cutter as it is slid back and forth along the groove. At the same time, the spindles act as guides in the vertical direction so as to guide the cutting surfaces of the rectilinear cutter downwardly as the exposed surfaces of the femur are progressively cut.

Further, in accordance with the preferred embodiment, the stem is provided with an attached but removable plastic portion (drill plate) that acts as a sacrificial member into which removable pins may be inserted through aligned holes drilled through the adjacent wall of the femur and into the sacrificial member after the stem is inserted into the femur, thus providing for the custom positioning of the stem. After each use, the sacrificial member may be removed from the principal body of the stem and a replacement attached, thereby rendering the stem repeatedly re-usable.

OBJECTS AND FEATURES OF THE INVENTION

It is one general object of the invention to improve equipment for definitively cutting the proximal end of a femur prior to cementing in a prosthesis.

It is another object of this invention to facilitate cleaning and re-use of equipment for cutting.

It is yet another object of this invention to provide for definitive cutting and preparation of the proximal end of a femur while minimizing damage to adjacent body tissue.

It is still another object of the invention to facilitate re-use of stems temporarily employed as supports for guides employed in preparing the proximal ends of femurs.

It is yet another object of this invention to provide improved methods for preparing the proximal ends of femurs for implantation of prostheses when employing serial pressurization of bone cement after the femoral stem has been inserted.

Accordingly, in accordance with one feature of the invention, an elongated prosthesis-like stem is provided with a relatively flat surface from which a first cylindrical removable spindle member extends essentially at right angles to the flat surface, the flat surface having a recess therein spaced a predetermined distance from the first spindle so as to receive a second spindle which is removable, the first and second spindles being essentially parallel so as to provide a pair of spaced guides for successive mounting of a rotational cutter in two positions, thereby providing for controlled dressing of a non-circular surface with a small diameter rotational cutter.

In accordance with another feature of the invention, the elongated prosthesis-like stem is provided with a replaceable sacrificial adjunct in a predetermined location into which drilling through the adjacent bone may occur whereby aligned drilled apertures are provided for temporary insertion of pins or the like thereby to temporarily and securely position the stem in the desired position within the femur, while providing for successive uses of the stem.

In accordance with yet another feature of the invention, provision is made for temporarily inserting a pin of predetermined cross-sectional geometry within the aforementioned recess, thereby providing a part of a mounting for a guide block which is adapted for mating with a rectilinear cutter.

In accordance with still another feature of the invention, the aforementioned first cylindrical spindle acts in cooperation with the aforementioned pin of predetermined cross-sectional geometry to secure the guide block in the desired position, thereby providing for coordinate cutting by the rectilinear cutter and the aforementioned rotational cutter.

In accordance with another feature of the invention, according to a preferred embodiment, the aforementioned rectilinear block is provided with an elongated rectilinear keyway slot extending therethrough, and the rectilinear cutter is provided with a mating longitudinally disposed keyway adapted for rectilinear movement within said keyway slot, thereby providing for guided precision linear movement of the cutter to perform rectilinear cutting of the prepared surface of the femur.

In accordance with yet another feature of the invention, the aforementioned rectilinear cutter is provided with a pair of planar cutting surfaces in angular relationship to each other, thereby providing for simultaneous rectilinear cutting in two different planes.

In accordance with still another feature of the invention, provision is made for adjusting the angle between the aforementioned pair of planar cutting surfaces, thereby imparting additional flexibility to the use of such cutter.

These and other objects and features of the invention will become apparent from the following detailed description, by way of a preferred example, with reference to the drawings.

BRIEF DESCRIPTION OF THE DRAWING

FIG. 1 is a partly sectioned side view of a positioning stem embodying the principles of the invention;

FIG. 2 is a perspective view of a guide block for use in practicing the principles of the invention;

FIG. 3 is a perspective view of a rectilinear cutter constructed in accordance with the invention;

FIG. 4 is a partly sectioned view depicting the positioning stem of FIG. 1 temporarily secured within a femur and a rotational cutter of the prior art rotationally mounted thereon;

FIG. 6 is a partly sectioned view similar to that of FIGS. 4 and 5 except with the rotational cutter of the prior art removed and with the guide block of FIG. 2 and the rectilinear cutter of FIG. 3 being lowered into place; and FIG. 7 is a view similar to that of FIG. 5 except showing the guide block and rectilinear cutter fully engaged with the positioning stem.

DESCRIPTION OF A PREFERRED EMBODIMENT

Figure 5:
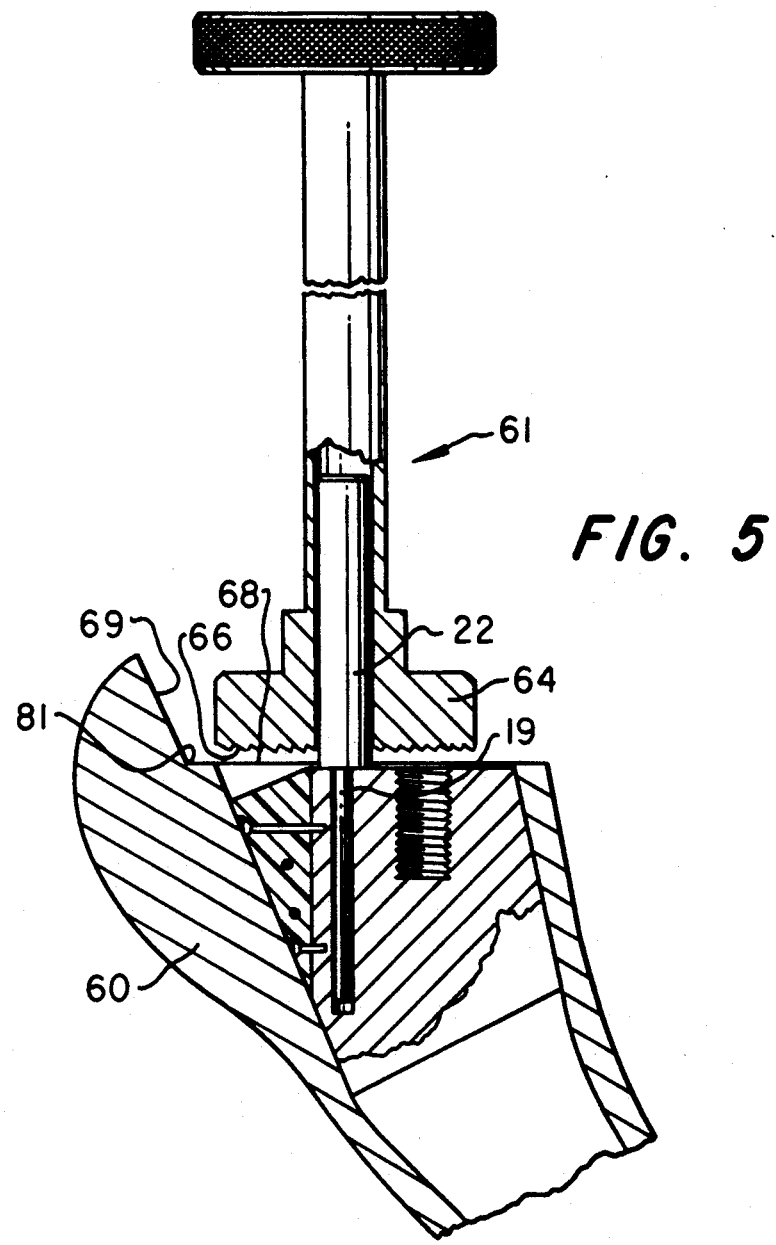
FIG. 5 is a partly sectioned view similar to that of FIG. 4 except depicting the rotational cutter of the prior art disposed a predetermined distance along the upper surface of the femur from that depicted in FIG. 4.

Now turning to the drawing, and more particularly FIG. 1 thereof, it will be observed that it depicts a stem positioning device 10 adapted for temporary insertion within a prepared cavity of a femur. The device 10 includes a lower stem portion 11 which is shaped to fit within the lower part of a femur cavity, and an upper stem portion 12 which is specially shaped for the practice of the principles of the invention.

Portion 12, shown as being partly cut away so as to facilitate illustration, includes sacrificial segment 13 which preferably is made of readily drillable plastic material. The remainder of stem 11 is preferably made of non toxic metallic material such as stainless steel or the like, although it may be formed of selected non-toxic non-metallic materials. Since the main body of stem 11 ordinarily is made of metallic material which is expensive, it is desirable to provide for the repeated use of the main stem body, and this is accomplished by the advantageous deployment of sacrificial segment 13 which is used as the target for custom drilling (and pinning, (e.g., by pins 56 and 57 in FIGS. 4-7) during positioning of the stem, and which can readily be replaced, thereby protecting the main body of stem upper portion 12 from drilling damage and rendering it repeatedly re-usable.

As will be evident to those skilled in the art, sacrificial member 13 can be removably attached to upper portion 12 by any of a variety of ways known in the art. Thus, member 13 can be fastened as by removable screws 14 and 14a which extend laterally from the outer surface 15 through member 13 and into mating recesses 16 and 16a within the outer surface 17 of upper portion 12. Preferably, removable screws 14 and 14a are countersunk so that their heads do not project outwardly beyond outer surface 15.

Further reference to FIGS. 4–7 reveals that the longitudinal axes of pins 56 and 57 are roughly at right angles to removable screws 14 and 14a, although other geometrical relationships could be employed. In practice, drilling is undertaken and the pins 56 and 57 inserted at and through the lateral aspect of the intertrochanteric area, then through the sacrificial member 13, and lastly through the medial cortex of the intertrochanteric area.

Referring again to FIG. 1, upper stem portion 12 includes a pair of recesses 19 and 20, one of which (recess 19) is un-threaded so as to accept the unthreaded portion 21 of positioning pin 22, and the other of which (recess 20) is threaded so as to accept the threaded portion 24 of positioning pin 25.

Ordinarily, positioning pin 25 is fastened in place by screwing its threaded portion 24 into the threaded portion 27 of recess 20; and in normal practice, positioning pin 25 remains attached to upper portion 12. However, should the need arise to disassemble pin 25 from stem 10 (as, for example, for replacement, cleaning or to provide for clearance between a cutter head positioned on pin 22 as hereinafter described), it can be unscrewed and removed.

Now turning to FIG. 2, it will be observed that it depicts the aforementioned guide block 30 which is adapted for use in practicing the principles of the invention. Guide block 30 includes an aperture 31 which extends entirely through block 30 along an axis essentially at right angles to planar upper surface 32. Aperture 31 is of a diameter essentially equal to that of positioning pin 25 so that positioning pin 25 will extend into and fit snugly within aperture 31. Downwardly projecting pin 33 depends from the lower surface 34 of guide block 30 and may either be detachable or an integral part thereof. However, when in use, pin 33 is rigidly affixed to the body of block 30 so as to act as an additional positioning pin therefor when block 30 is mated to stem positioning device 10.

Extending longitudinally and rectilinearly along the side 35 of block 30 is keystone-shaped slot 36 which is of uniform cross-section so as to facilitate its use as a guide and retainer for keystone-shaped mating part 41 of rectilinear cutter 40 (FIG. 3) which is constructed in accordance with the invention. As will be observed, lower surface 37 of slot 36 (FIG. 2) engages mating surface 37a (FIG. 3), rear surface 38 of slot 36 (FIG. 2) engages mating surface 38a (FIG. 3), and upper surface 39 of slot 36 (FIG. 2) engages mating surface 39a (FIG. 3) of rectilinear cutter 40. When in use, such engagement is occasioned by sliding either end of mating part 41 into the corresponding end of slot 36. Since the exterior dimensions of keystone-shaped mating part 41 are only sufficiently less than the corresponding dimensions of mating slot 36 so as to permit smooth sliding movement, block 30 acts as a precision guide to guide the lateral linear movement of cutter 40 when cutter 40 is engaged therewith.

Further reference to FIG. 3 reveals that cutter 40 is fitted with a handle 42 so as to provide a ready means of grasping the cutter and for controllably sliding cutter 40 back and forth rectilinearly when cutter 40 is engaged with guide block 30.

Cutter 40 is seen to include the main body 43 which has the aforementioned keystone-shaped mating part 41 as well as lower support section 44. Lower support section 4 includes a longitudinally extending notch 45 adapted for receiving and holding a lower rasp member 46 which, at its lower surface 47, is fitted with rasp teeth or irregularities 48. Cutter 40 is seen also to include a pair of bent straps 49 and 49a which are bent at predetermined angles and which affix upper rasp assembly 50 to main body 43 by the use of four screws 51a–51d. Screws 51a and 51c affix the rear portions of straps 49 and 49a to main body 43; and Screws 51b and 51d pass through aligned apertures (not shown) extending through each of the individual saw blades 52a–52n of saw blade stack 52. As will be observed from further inspection of FIG. 3, the lowest blade 52n of saw blade stack 52 lies in contiguous relationship to a surface 53 of main body 43 and is held in place thereat by screws 51b and 51d.

Lower rasp member 46 may be any of a number of members well known in the art such as a small common rasp of the type generally sold in hardware stores, a file, or the like, made of material such as steel, stainless steel, or other similar materials that are non-contaminating and corrosion resistant. The rasp should have small and relatively short teeth so as to be compatible with the femur and not to break the thin cortical wall in the region undergoing preparation.

Upper rasp member assembly 50 preferably is constructed from a plurality of band saw blade sections or a plurality of hacksaw-type blade sections preferably with about 14 teeth to the inch. Again the blades are preferably made of stainless steel, monel or other similar materials that are non-contaminating and corrosion resistant. These blades are assembled into the stack 52 by placing the blades in side-by-side relationship as shown in FIG. 3, with their cutting edges exposed as at surface 54. Assembly 50 may also be constructed of a section of a suitable rasp.

It will now be seen that rectilinear cutter 40, when assembled as shown in FIG. 3, exhibits two essentially planar cutting surfaces, surface 47 of lower rasp member 46, and surface 54 of stack 52. It will also be evident that these two essentially planar cutting surfaces are disposed in predetermined angular relationship with respect to each other and that such angular relationship can be readily changed by interchanging straps 49 and 49a with similar straps having the desired degree of angular bending. It will also be evident that a corresponding change in the effective angular disposition of surface 53 of main body 43 can be effected by disposition thereon of a triangular wedge of appropriate geometry. Accordingly, provision is made for the coordination of cutting with implements used in subsequent operative steps such as the angle at the posterior inferior surface of the separator-sealer described in my U.S. Pat. No. 4,357,716.

Now turning to FIG. 4, it will be evident that it depicts stem positioning device 10 temporarily installed in place within a prepared femur 60. Positioning pin 52 is shown installed in place, and a conventional circular cutter assembly 61 is shown temporarily mounted on positioning pin for rotation around the central axis thereof.

Conventional circular cutter 61 is well known in the art. Although any of a variety of such cutters may advantageously be employed in practicing the principles of the invention, a suitable cutter is that which is known as an intertrochanteric cutter. Such cutters are sold commercially and are available from the Zimmer Manufacturing Company of Warsaw, Ind.

As will be sen from further inspection of FIG. 4, the cutter comprises a knurled circular operating handle 62 mounted on circular shaft 63 which imparts circular torque manually applied through handle 62 to the cutter head 64.

It will be observed that the cutter head 64 and circular shaft 63 includes a cylindrical recess 65 such that the cutter assembly 61 can be positioned as shown onto positioning pin 25 about which it rotates and which serves as a guide for ensuring that cutting surface 66 will contact a desired first portion 67 of the upper (proximal) surface 68 of femur 60.

The principles according to the invention embody flexibility in their application. Thus, FIG. 5 illustrates an embodiment in which the conventional rotational cutter assembly 61 is moved laterally along the proximal surface of femur 60 from the position depicted in FIG. 4 so as to extend laterally the upper surface of femur 60 with which its cutting surface 66 becomes engaged. This is accomplished by inserting positioning pin 22 into recess 19 after removing positioning pin 25 (FIG. 4). However, the principles of the invention may be utilized without a second use of conventional cutter assembly 61 for, as will be evident from the description below, the use of rectilinear cutter 40 (FIG. 3) may follow the first use of conventional cutter assembly 61 without the intervening use of assembly 61 positioned on positioning pin 22. However, according to the preferred embodiment, the radius of cutter head 64 is no greater than 1/64th of an inch of the distance from the center of recess 19 to corner 81 that lies at the intersection of surfaces 68 and 69. Thus, any slight irregularity existing at or immediately adjacent corner 81 can readily be removed when rectilinear cutter 40 is employed as described below.

As shown in FIG. 6, following the use of conventional circular cutter assembly 61, positioning pin 25, if previously removed, is reinstalled and guide block 30 is mounted thereon, with the upper end of pin 25 extending into mating aperture 31. Coincident therewith, downwardly projecting pin 33 of guide block 30 extends into mating recess 19, thereby providing two attachments and resulting in a stable orientation of guide block 30 with respect to stem positioning device 10. The keystone-shaped mating part of rectilinear cutter 40 is then slid into its mating keystone-shaped slot on block 30, and rectilinear cutter 40 is then in position and ready for employment. As previously mentioned, such employment is used to impart a precision dressing to surfaces 68 and upper inclined surface 69 of femur 60.

It will be evident from an inspection of FIG. 6, that prior to use of rectilinear cutter 40, the plane of the surface 54 of cutter 40 is at an angle with respect to the plane of the upper inclined surface 69 of initially prepared femur 60. As block 30 is lowered and as cutter 40 is moved back and forth longitudinally, cutting surface 54 engages surface 69 and cuts the same until surface 69 takes the shape 69a illustrated in FIG. 7. Also, when lower surface 47 of lower rasp member 46 engages upper surface 68 of femur 60, it cuts and smooths a predetermined amount of the upper surface 68, an amount determined by the downward distance that block 30 can travel until its lower surface 34 engages the adjacent surface 70 of stem positioning device 10.

One of the advantages of the rectilinear cutter 40 as described herein derives from its adaptability for use with conventional powered apparatus which may be connected at either or both ends. Thus, further reference to region 41 (FIG. 3) reveals region 41a which may be adapted for engagement with the output of any of a variety of rectilinear motion imparting power equipments (not shown) that are well known in the art. By using a reciprocating power source, the cutter will perform the desired cutting action as the operator slowly moves the rectilinear cutter from one end to the other within its track in the above-described keystone-shaped guide, thereby allowing bone chips between teeth to fall out while adjacent clean or cleared teeth are actively cutting. Moreover, as a consequence of the above-described geometries, the cutter lends itself to cooperation with a reciprocating power source for preparation for either a right or left hip. Of course, it will be self-evident that a region corresponding to region 41a exists at the opposite end of region 41, thereby rendering the cutter adaptable for use with a reciprocating power source engaged at either end.

After employment of cutter 40, the apparatus according to the invention is disengaged from femur 60. Guide block 30 and rectilinear cutter 40 may be simply lifted upwardly so as to disengage pins 33 and 25 after which cutter 40 may be slid laterally to become disengaged from block 30. Alternatively, cutter 40 may be first disengaged from block 30, after which block 30 can be lifted upwardly.

The stem positioning device 10 is removed from its secured position within femur 60 by removing pins 56 and 57, after which it may be grasped and lifted vertically to withdrawn it therefrom.

Since, as mentioned above, sacrificial segment 13 is readily replaceable, stem positioning device 10 can be repeatedly used. This is accomplished by removing removable screws 14 and 14a, discarding sacrificial segment 13, and installing a replacement. Of course, the assembly must be thoroughly sterilized between uses so as to prevent the transmission of contamination of disease-producing bodies from one patient to another.

It will now be evident that there has been described herein, an improved method and apparatus for preparing a femur for installation of a prosthesis. Although the invention hereof has been described by way of example of a preferred embodiment, it will be evident that other adaptations and modifications can be employed without departing from the spirit and scope thereof. For example, a non-threaded pin could be utilized in place of positioning pin 25.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. Apparatus for definitive cutting of the proximal end of a femur prior to cementing in a prosthesis comprising:

(a) an elongated prosthesis stem having a pair of opposed ends, one of said ends having at its termination, an essentially flat surface lying within a plane essentially at right angles to the adjacent longitudinal axis of said stem; said essentially flat surface having extended therefrom a pair of elongated cylindrical members having parallel axes, said axes being essentially at right angles to said essentially flat surface;

(b) a block adapted for detachable mounting on said elongated cylindrical members, said block having an elongated keyway slot disposed therein, said keyway slot having a principal longitudinal axis lying essentially at right angles to said parallel axes when said block is mounted on said cylindrical member; and (c) a rectilinear cutter having a principal linear axis, said rectilinear cutter having on one surface thereof a projecting longitudinally disposed keyway of geometry and cross section adapted for mated fitting within said keyway slot thereby to slideably retain said keyway within said keyway slot while permitting longitudinal movement therebetween.

2. Apparatus according to claim 1 in which said elongated prosthesis stem includes adjacent said one of said ends, a sacrificial portion of said stem comprised of plastic and adapted for drilling and receiving pins to temporarily rigidly affixed said stem in position within a femur.

3. Apparatus according to claim 1 in which said rectilinear cutter includes an operating handle extending from said cutter in a direction essentially perpendicular to said principal linear axis of said cutter.

4. Apparatus according to claim 1 in which said block includes a pair of cylindrical recesses adapted for mating with and receiving therewithin said pair of elongated cylindrical members.

5. Apparatus according to claim 4 in which said pair of cylindrical recesses are adapted for slideable mating with said pair of elongated cylindrical members, thereby to permit slideable movement of said block with respect to said stem.

6. Apparatus according to claim 1 in which said essentially flat surface includes therein a cylindrical recess for receiving and affixing one of said pair of elongated cylindrical members.

7. Apparatus according to claim 6 in which said cylindrical recess includes internal threads.

8. Apparatus according to claim 7 in which said one of said pair of elongated cylindrical members is partially threaded with threads adapted for threaded engagement with said internal threads.

9. Apparatus according to claim 1 in which said block is slideably mounted on said elongated cylindrical members.

10. Apparatus according to claim 1 in which said rectilinear cutter includes two separated cutting surfaces lying in different planes.

11. Apparatus according to claim 10 in which said different planes are angularly disposed at an angle greater than 90 degrees.

12. Apparatus according to claim 10 in which said rectilinear cutter includes a planar surface parallel to said principal linear axis, said planar surface being disposed adjacent one of said cutting surfaces for contacting a part of said essentially flat surface when cutting has progressed a predetermined amount.

13. Apparatus according to claim 1 further including a reciprocating power source, and wherein said rectilinear cutter includes a predetermined region at one end of said principal linear axis adapted for engagement with said reciprocating power source.

14. Apparatus according to claim 1 further including a reciprocating power source, and wherein said rectilinear cutter includes a pair of predetermined regions at opposite ends of said principal linear axis adapted for manual engagement and for engagement with said reciprocating power source.

15. A method of definitively cutting the proximal end of a femur prior to cementing in a prostheses comprising:

(a) making an initial rough cut of the antero-medial aspect of the femur thereby to expose the femoral canal of said femur;

(b) preparing said femoral canal of said femur to temporarily receive a prosthesis stem;

(c) inserting said prosthesis stem within said femoral canal;

(d) using a projection from said prosthesis stem as a first spindle for rotationally cutting a portion of the antero-medial aspect of said femur;

(e) mounting on said projection a rectilinear cutter; and (f) activating said rectilinear cutter to produce a rectilinear cut on the intertrochantic area of said femur.

16. The method according to claim 15 further including using a second projection from said prosthesis stem as a second spindle for rotationally cutting another portion of the intertrochantic area lying in the same plane as that made by the cylindrical cutter on said first spindle.

17. The method according to claim 16 further including mounting said rectilinear cutter on said first and second spindles.

18. The method according to claim 16 in which activating said rectilinear cutter to produce a rectilinear cut includes moving said cutter progressively along said projection and said second projection thereby to retain said cutter in contact with said intertrochantic area of said femur as the intertrochantic area of said femur is progressively cut.

19. The method according to claim 16 further including drilling holes laterally through the walls of said femur and into said prosthesis stem after said prosthesis stem has been inserted within said femoral canal.

20. The method according to claim 19 further including inserting pins through said holes to temporarily affix said prosthesis stem in place within said femoral canal.

21. The method according to claim 15 in which activating said rectilinear cutter to produce a rectilinear cut includes moving said rectilinear cutter reciprocatingly along a linear axis.

22. The method according to claim 15 in which activating said rectilinear cutter to produce a rectilinear cut includes moving said cutter progressively along said projection until the advancing edge of said cutter lies in the plane which was defined by said first circular cutter.

* * * * *